United States Patent [19]

Tanaka et al.

[11] 4,352,018

[45] Sep. 28, 1982

[54] APPARATUS FOR PERFORMING POSITRON EMISSION COMPUTED TOMOGRAPHY

[75] Inventors: Eiichi Tanaka, Mitaka; Norimasa Nohara, Chiba; Takehiro Tomitani, Chiba; Mikio Yamamoto, Chiba; Kenji Ishimatsu, Abiko; Katsumi Takami, Tokyo, all of Japan

[73] Assignees: National Institute of Radiological Sciences, Chiba; Hitachi Medical Corporation, Tokyo, both of Japan

[21] Appl. No.: 133,895

[22] Filed: Mar. 25, 1980

[30] Foreign Application Priority Data

Mar. 30, 1979 [JP] Japan .................................. 54-36860

[51] Int. Cl.³ .................... G01T 1/20; G01N 21/00
[52] U.S. Cl. .................... 250/363 S; 250/366; 378/4
[58] Field of Search .............. 250/363 S, 366, 369, 250/445 T

[56] References Cited

U.S. PATENT DOCUMENTS

| | | | |
|---|---|---|---|
| 3,970,853 | 7/1976 | Kuhl et al. | 250/363 S |
| 4,150,292 | 4/1979 | Ter-Pogossian | 250/363 S |
| 4,213,054 | 7/1980 | Doherty et al. | 250/445 T |
| 4,259,578 | 3/1981 | Thompson | 250/363 S |

*Primary Examiner*—Alfred E. Smith
*Assistant Examiner*—Janice A. Howell
*Attorney, Agent, or Firm*—Gerald J. Ferguson, Jr.; Joseph J. Baker

[57] ABSTRACT

An apparatus for effecting positron emission computed tomography comprises rows of a plurality of arrays of detectors arranged rotatably around a center of rotation in such way that at least one of the detectors in each array is disposed at an irregular position relative to the rest of detectors in the array, and that, for each revolution of the row through an angle of 360°/n (wherein: n represents an odd number of 3 or larger), each array of detectors will assume exactly the position occupied by its adjacent array till the revolution takes place.

5 Claims, 22 Drawing Figures

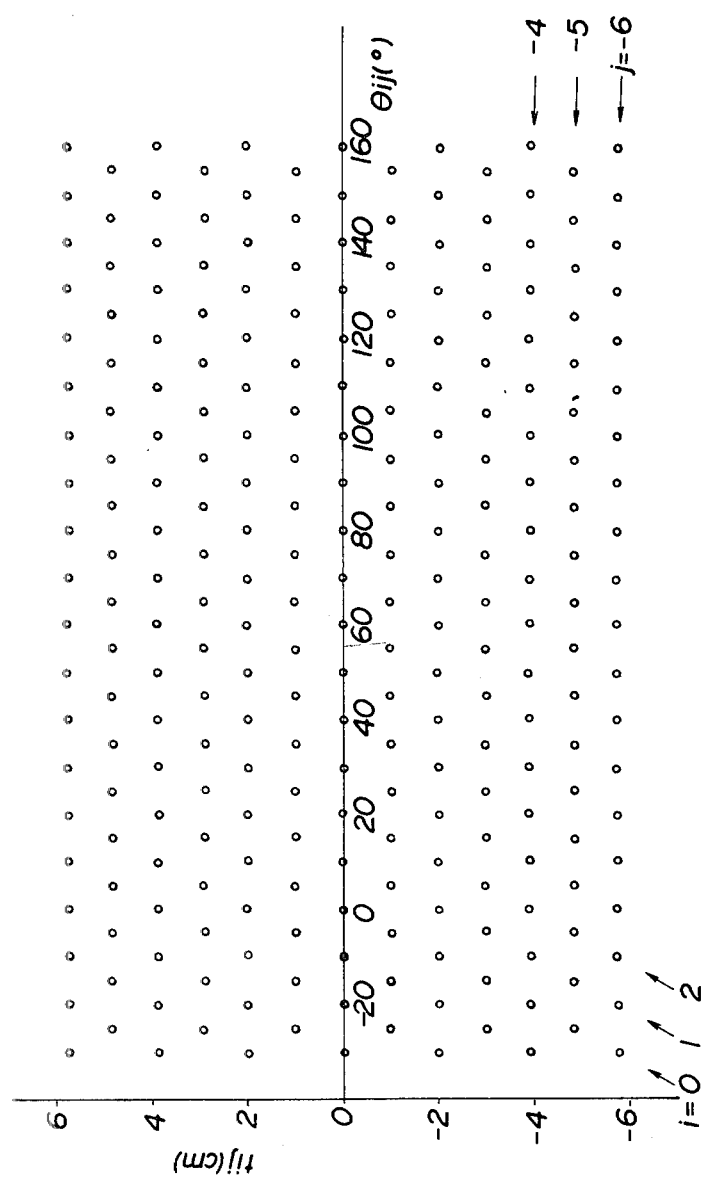

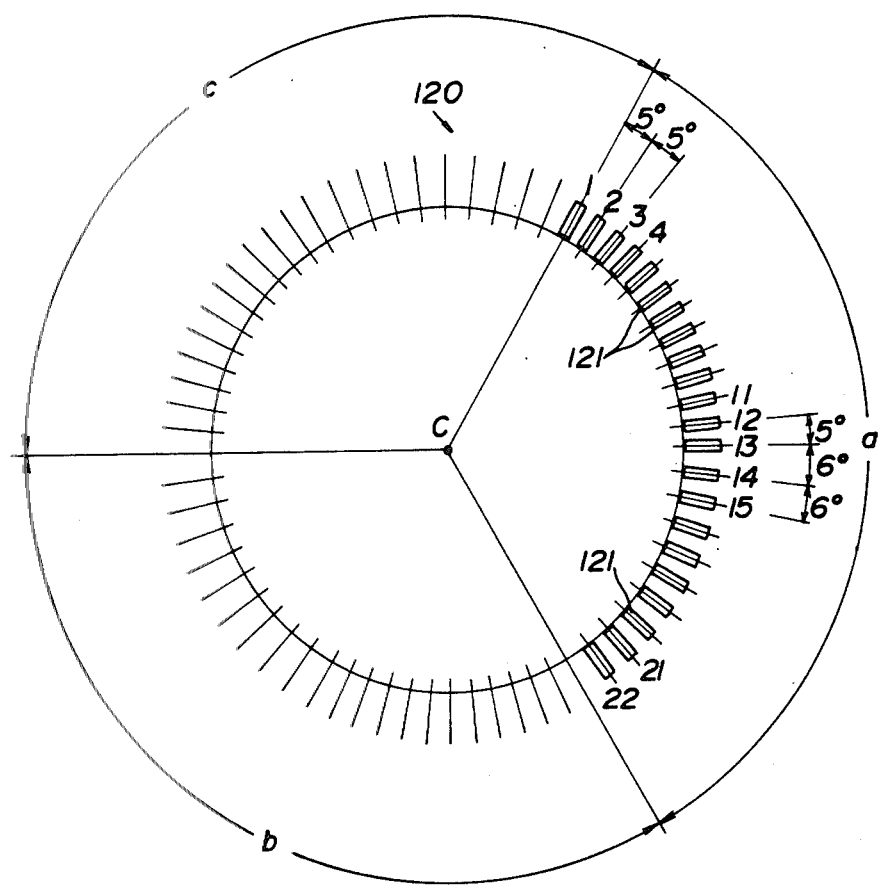

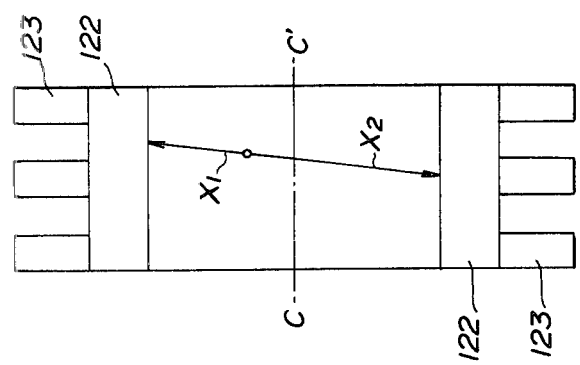
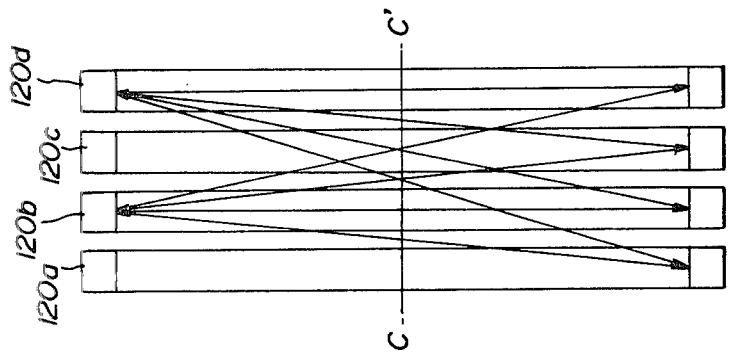
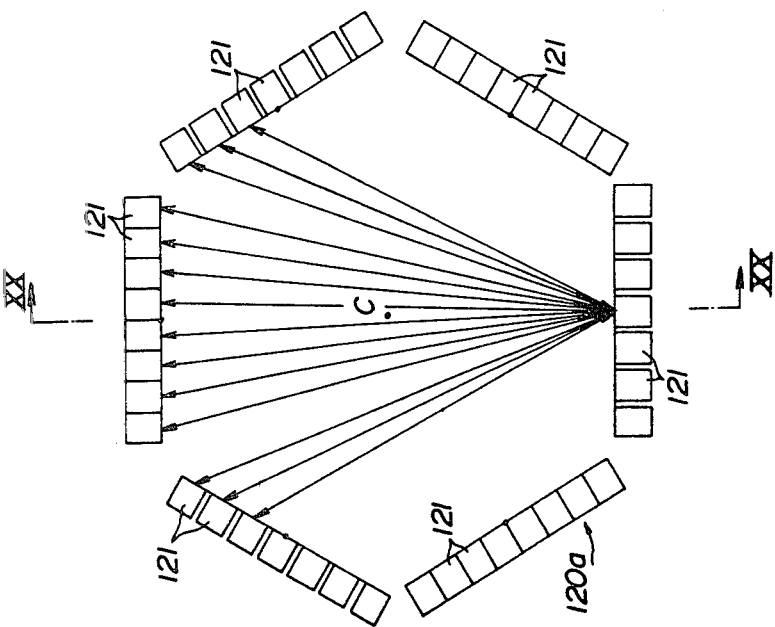

APPARATUS FOR PERFORMING POSITRON EMISSION COMPUTED TOMOGRAPHY

BACKGROUND OF THE INVENTION (a) Field of the Invention

The present invention concerns an apparatus for performing positron emission computed tomography, and more particularly it pertains to an improvement of the arrangement of the detectors employed in this apparatus.

(b) Description of the Prior Art

There have been proposed apparatuses for effecting a measuring, externally of the subject to be examined, of intra-body distribution of positron-emitting radioisotopes which are administered into the body of the subject, and those apparatuses designed for displaying images of a slice on a cathode ray tube.

FIG. 1 schematically shows the principle of such known apparatus. In FIG. 1, reference numeral 1 represents a subject for examination. 2 represents respecrive gamma ($\gamma$) ray detectors (hereinafter to be referred to briefly as detectors). 3 represents an array of detectors which is constructed by a row of a plurality of detectors. 4 represents a coincidence counting circuit. 5 represents a data collecting and recording means. 6 represents a data processing means. 7 represents an image display means. The detectors included in the array 3 of detectors are disposed on a plane containing a slice of the subject 1 for examination which is to be displayed, and these detectors are assigned to detect gamma rays due to the isotopes contained in the body of the subject 1.

The isotope which is administered into the body of subject 1 is selected from those substances, such as carbon 11 ($^{11}C$), nitrogen 13 ($^{13}N$) and fluorine 18 ($^{18}F$) which emit positrons. Positrons which are emitted from atomic nuclei of the isotopes cause annihilation reaction with the electrons which are present at sites very close to those positrons emitted. As a result, there are generated two annihilation gamma photons which are emitted in opposite directions (in the directions of 180°) at the same time. Let us now suppose that two of the detectors 2, each representing one in the respective arrays 3 of detectors which are provided on both sides of the subject 1 in FIG. 1 have detected annihilation gamma photons at the same time. Then, the positions at which these annihilation gamma ray photons are generated, i.e. approximately the positions of the isotope atoms which have emitted positrons, are considered to be on the straight line connecting these two detectors. It should be understood that each of those solid lines connecting two detectors which are contained in the respective arrays 3 of detectors represents an imaginary straight line passing through the position of the isotope atom which is found by detecting the coincidence count performed by the two detectors connected by that straight line. The abovesaid imaginery straight line indicating the position of the isotope atom which is found out can be designated by the positional coordinate of the opposing two detectors which participate in the coincidence counting. It should be understood, however, that such position of the isotope atom which is found out may be designated also by the two factors, i.e. the distance t from the origin of an appropriate coordinate system which is fixed in the subject 1 and which lies in a plane containing the arrays 3 of detectors to the aforesaid imaginary rectilinear line and which has the coordinate origin at the center of rotation, and the angle $\theta$ defined by this imaginary rectilinear line relative to an axis of coordinate. In this specification, the position of the isotope atom which is detected is represented by a rectilinear line connecting two detectors, and it is expressed by the distance t and the angle $\theta$, and such position is called a sample position or sampling position, and the aforesaid two detectors which are electrically connected by a coincidence counting circuit for detecting a coincidence count are called a detecror pair. The emission of positron which is thus detected by an appropriate detector pair connected together by a coincidence counting circuit is recorded of its number of count and sampling position (t, $\theta$), by a data-collecting-and-recording means 5. Those data which thus have been recorded within a certain period of time are then subjected to rearrangement and reconstruction of the data at a data processing means 6, whereby an image of distribution of isotopes in that portion of the body of subject which is sliced at said plane, i.e. a cross-sectional image, is synthesized, and it is displayed by an image indicating means 7.

FIG. 2 shows an arrangement of detectors in a known scanner for positron emission computed tomography which is based on the foregoing principle. In FIG. 2, there are depicted thirty six (36) detectors to facilitate understanding. It should be noted, however, that in practice there are arranged 60~200 detectors. It this known apparatus, detectors 2 are arranged with equal spacing on a circular circumference surrounding the subject 1, and these detectors are connected to coincidence counting circuits for detecting coincidence counts between them and those detectors which are located on the other side relative to the center C of the circular circumference. It should be understood that a certain detector located on this side is not coupled to only one detector located on the other side to make a pair, but to a plurality of detectors via a coincidence counting circuit. All of those detectors which are located on the other side relative to a certain designated detector located on this side, and which are located within the range of coverage by this certain detector are coupled to this certain detector by coincidence counting circuits, respectively. For example, the certain designated detector is coupled, by coincidence counting circuits, to all of those detectors which lie within an angle ±30° as viewed from this certain detector relative to the rectillinear line connecting this certain detector and the center C of the aforesaid circular circumference.

A scanner of the known apparatus having such arrangement of detectors as stated above is capable of making detection as well as coincidence counting of those gamma ray pairs which are emitted at arbitrary positions lying within a circle of a radius which is about ½ of the radius of the circular circumference on which the detectors are arranged, without requiring mechanical movement such as rotation of the arrays of detectors, and thus the scanner is able to determine their sampling positions (t, $\theta$).

In such known apparatus, the values of t which are obtained represent discontinuous descrete values having distance intervals substantially equal to the spacing of the detectors. On the other hand, the values of $\theta$ obtained are only discontinuous discrete values with intervals representing an angle defined by a detector and adjacent two detectors which are located on the other side relative to the center C. Apart from the above, the smaller the respective intervals of the values t and of the values θ are, the higher can be improved the quality of the image which is reconstructed. Thus, with such known apparatus, it is not possible to obtain intervals of t or θ which are sufficient for obtaining a quality image. Also, if a large number of detectors are arranged to make the intervals of θ or of t sufficiently small, it will be obvious that the cost of manufacture will be increased markedly.

On the other hand, there has been proposed to improve the quality of image, in this known apparatus, by first taking a measurement once at a stationary state of the apparatus, and thereafter repeating the measurement after revolving the arrays of detectors through an angle which is ½ of the angle defined by the center C and adjacent two detectors located on one side relative to this center C, thereby making the respective intervals of t and of θ½ relative to the intervals obtained at the time of measurement at stationary state of the arrays of detectors. It should be understood, however, that even from further continuation of such revolution, it is not possible to reduce the intervals of t and of θ any further. Furthermore, even when a measurement is taken by making the angle of one revolution sufficiently small, there will arise no change in the intervals of t which control the resolution of image, though the intervals of θ will become reduced accordingly.

Description will hereunder be made of the manner of expressing the fineness of the sample positions, in order to facilitate the understanding of the present invention.

In FIG. 3, point C and the rectilinear line XX represent the origin and the coordinate axis of the coordinate system which is fixed to the body of the subject for examination. The array of gamma ray detectors is rotated about this point C. Point i and point j represent appropriate gamma ray detectors which make a pair among the array of detectors. $r_i$ and $r_j$ represent the distances from the center C of rotation of the detectors i and j. $a_i$ and $a_j$ represent angles defined by $r_i$ and $r_j$ relative to the axis of coordinate axis XX. $t_{ij}$ and $\theta_{ij}$ represent the distance from point C to the rectilinear line connecting the detectors i and j, and the angle formed by this rectilinear line relative to the coordinate axis XX, i.e. the sampling position of the information obtained by the coincidence counting by the detector pair i and j, respectively. Let us now assume that, with respect to all angles, those angles going counter-clockwise are designated as positive angles, and that those going clockwise are designated as negative angles. Then, the sampling positions $\theta_{ij}$ and $t_{ij}$ of an arbitrary detector and obtained, based on FIG. 5, by the below mentioned formulas:

$$\theta_{ij} = \tan^{-1} \frac{r_i \sin a_i - r_j \sin a_j}{r_i \cos a_i - r_j \cos a_j} \quad (1)$$

$$t_{ij} = -r_i \sin(\theta_{ij} - a_i) \quad (2)$$

It is to be noted here that the chart in which $\theta_{ij}$ and $t_{ij}$ in Formulas (1) and (2) are expressed in a single chart for all the detectors will hereunder be called the t, θ distribution chart.

FIG. 4 is a chart of distribution of t and θ, in the instance wherein the known apparatus shown in FIG. 2 is not rotated. In FIG. 4, the vertical axis represents distance t, and the horizontal axis represents angle θ, and the respective sampling positions (t, θ) are shown by small circles. These Figures are provided so that, for the convenience of calculation, the spacing between the detectors is selected at 2 cm and the radius of this aforesaid circle is selected at about 11.5 cm. Also, the visual angle of each detector is set so as to be ±30°. As will benoted from FIG. 7, in the known apparatus, the interval of t at sampling points where θ is identical, in case the detectors are not rotated, is equal to the spacing of 2 cm between the detectors in the central portion, whereas in the peripheral portion, i.e. in the region where t is large, the interval of t will become slightly smaller than the spacing between the detectors. Also, in case the array of detectors is rotated through an angle of 5° relative to the center C of the circle, i.e. in case the array of detectors is rotated through an angle which is ½ of the spacing between the detectors, and in case data are collected before and after such rotation, the sampling points of the data in this latter case will be exhibited as those obtained by translating or moving the distribution of the former by 5° for the horizontal axis. Accordingly, as will be noted from the Figure, the interval of t when θ is identical will become ½ of that obtained when the detectors are not rotated. However, even when a further rotation is made, the result is that sampling points are merely superposed, and it is not possible to reduce the interval of t.

The known apparatus which is called PETT 1 (H. J., De Blanc and J. A. Sorenson (ed.); Noninvasive Brain Imaging: Computed Tohography and Radionuclides, the Society of Nuclear Medicine, Inc., New York, 1975 pp 87-109) adopts the method such that, as shown in FIG. 5, four detectors are disposed at an equal interval on each side of a regular hexangle cocentral with the center of rotation, so that coincidence counting is carried out between those detectors located on the opposing two sides, for example, a-a' of the regular hexangle. Furthermore, in this known apparatus, the respective lines, $O_1-O'_1$, $O_2-O'_2$ and $O_3-O'_3$ connecting the centers of the respective arrays of opposing two sides of the hexangle are arranged to be at different distances, respectively, from the center of rotation, so as to be operative that, by rotating the detectors through 360°, those values of t of the sample positions which are produced by the detector pairs a-a', b-b' and c-c' are different relative to each other. In this known apparatus, however, those detectors in the respective arrays are disposed at an equal interval, and accordingly, when a single detector is considered, conincidence counting is carried out between it and only those detectors which are disposed at an equal interval, so that no sufficient distribution of the values of t of the sample position is obtained.

SUMMARY OF THE INVENTION

It is, therefore, an object of the present invention to seek an apparatus for effecting positron emission computed tomography, which is arranged so that, by rotating the arrays of detectors, the distance to of the sample position (t, θ) can take a number of different values.

Another object of the present invention is to provide the apparatus of the type described above, which is arranged so that arrays of a plurality of detectors at least one of which in each array is disposed at an irregular position relative to the remainder detectors of said array are provided around the center of rotation in such way that each array will assume, for each revolution of the arrays through an angle of 360°/n (wherein: n represents an odd number of 3 or greater), exactly the same position which has been occupied by its adjacent array until such revolution takes place.

BRIEF DESCRIPTION OF THE DRAWINGS

FIG. 4 is a diagram showing the distribution of sample positions obtained by the arrangement of the arrays of detectors shown in FIG. 2.

FIG. 10 is an explanatory illustration showing an example of the arrangement of arrays of detectors according to the present invention.

FIG. 20 is an explanatory illustration showing a still further arrangement of arrays of detectors, embodying the present invention.

FIG. 21 is an explanatory illustration showing a section of the array of detectors taken along the line XXI—XXI in FIG. 20.

FIG. 22 is an explanatory illustration of a yet further arrangement of arrays of detectors, embodying the present invention.

DETAILED DESCRIPTION OF THE PREFERRED EMBODIMENTS

Figure 1:
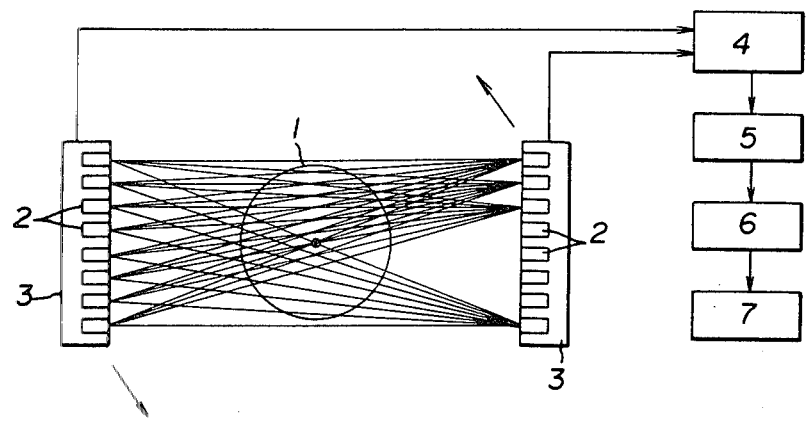
FIG. 1 is a diagram for explaining the general construction of a positron emission computed tomography apparatus.
Figure 2:
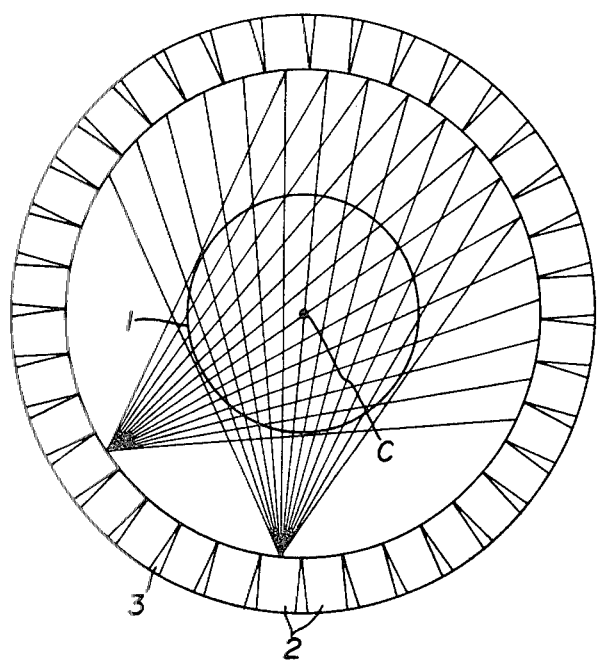
FIG. 2 is an diagrammatic explanatory illustration showing an example of the arraying of detectors in a known apparatus for effecting positron emission computed tomography.
Figure 3:
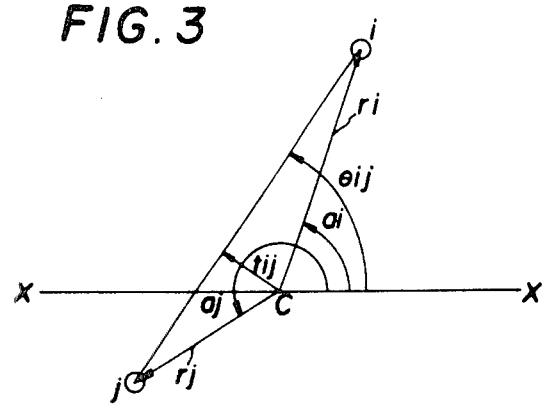
FIG. 3 is a diagram for explaining sample positions (t, θ), in an apparatus for effecting positron emission computed tomography.
Figure 5:
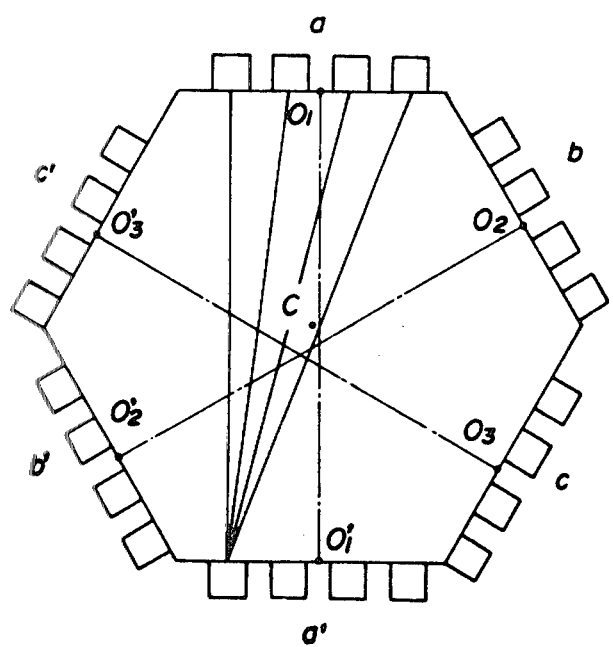
FIG. 5 is an explanatory illustration showing the arrangement of arrays of detectors in another known apparatus for effecting positron emission computed tomography.
Figure 6:
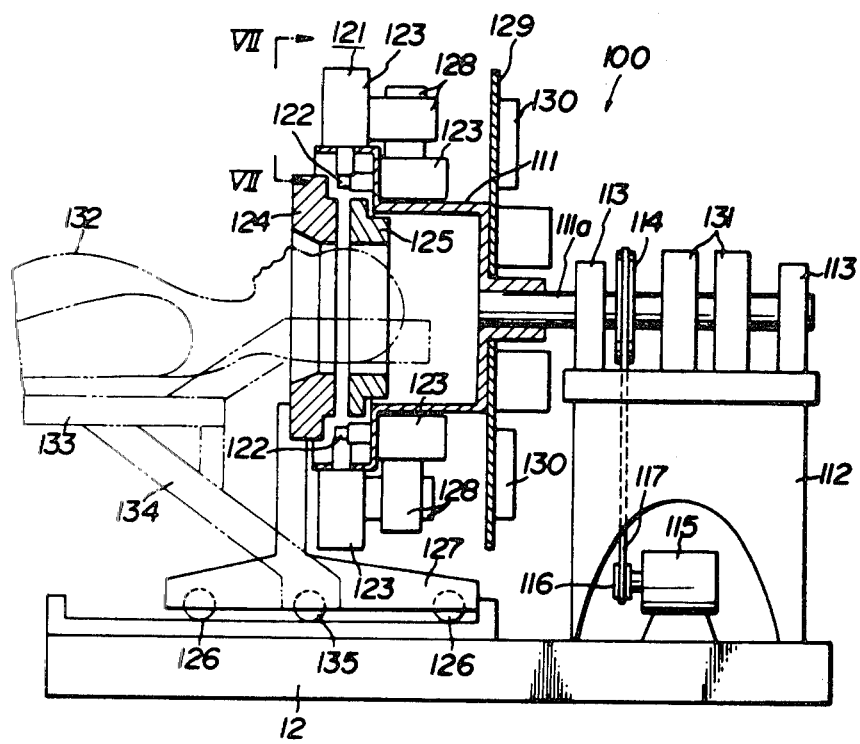
FIG. 6 is a diagrammatic sectional view showing an embodiment of the apparatus for effecting positron emission computed tomography according to the present invention.
Figure 7:
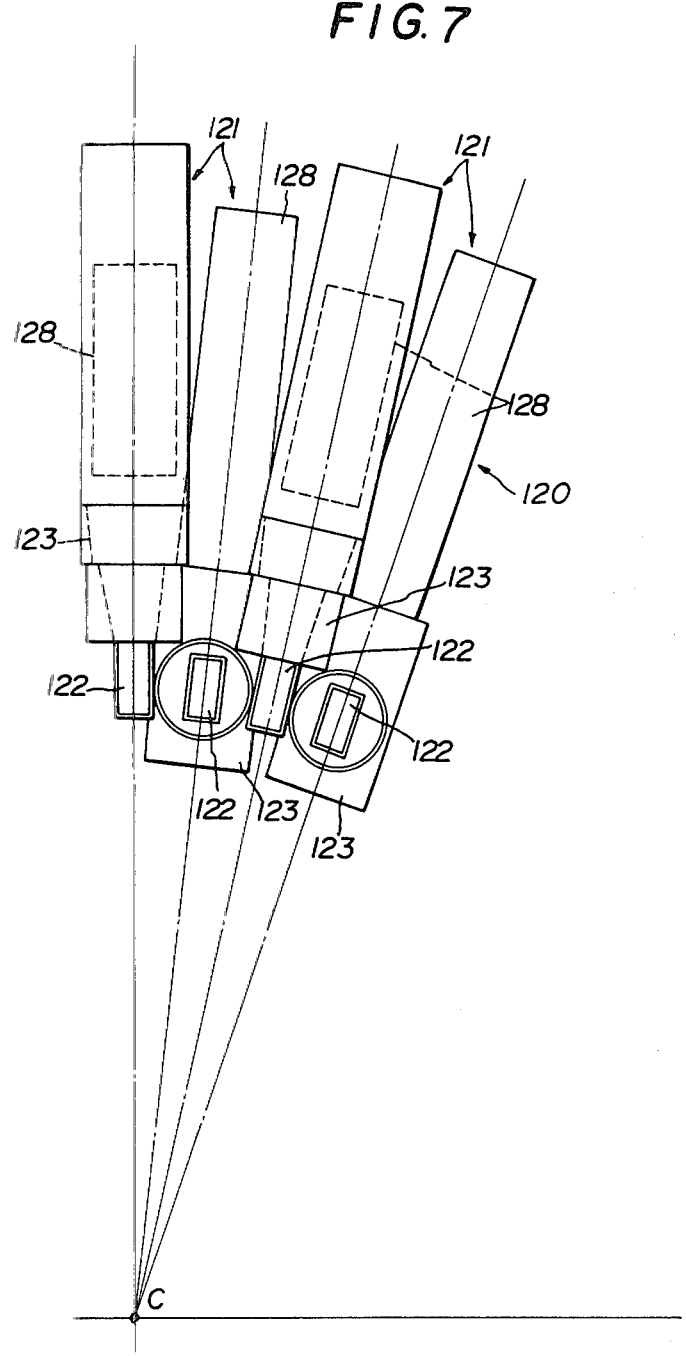
FIG. 7 is a diagrammatic enlarged front view of a part of an array of detectors taken along the line VII—VII in FIG. 6.

FIGS. 6 and 7 show an example of concrete structure of the apparatus for effecting positron emission computed tomography according to the present invention. The apparatus 100 has a rotary frame 111. This rotary frame has a body which is substantially hollow cylindrical configuration. A side plate is fixed to one of the open ends of this body. A shaft 111a is received in and fixed to, at its one end, this side plate. The opposite end portion of this shaft is supported on a bearing 113 which is provided on a pedestal 112. A belt-pulley 114 is mounted on the shaft 111a. This belt-pulley 114 is coupled, by a timing belt 117 such as a synchronous drive belt, to a belt-pulley 116 which is mounted on a rotary shaft of an electric motor 115 provided on the pedestal, so that the rotary frame is adapted to be rotated by the electric motor.

A detecting unit 120 is comprised of a number of gamma ray detectors 121 arranged along the circumference of the rotary frame 111. The respective gamma ray detectors of the unit are each comprised of a scintillator 122 and a photomultiplier tube 123, so that the scintillator is adapted to emit fluorescent light by the irradiation of gamma ray thereto, and that the photomultiplier tube is adapted to output a pulse which is proportional to the intensity of the fluorescent light. The respective scintillators are arranged so that they are located in an imaginary plane or slice plane which intersects, at right angle, the central axis C of rotation of the rotary frame 111. In this apparatus, the photomultiplier tubes of any adjacently located detectors are arranged, as will be best seen in FIG. 7, to cross each other at right angle, so that gamma ray detectors can be disposed close to each other, that the gamma ray detection sensitivity is enhanced, and that the device as a whole is constructed compact. A collimator is comprised of two ring-shaped members 124 and 125. These two ring-shaped members are disposed to oppose each other to form a gamma ray passageway, and are supported on a stand 127 having wheels 126. The respective gamma ray detectors are electrically connected to pre-amplifiers 128 which, together with these gamma ray detectors, are provided on the rotary frame 111. The respective pre-amplifiers are connected to coincidence counting circuits 130 which are provided on a supporting plate 129 which, in turn, is fixed to the rotary frame, in such way that each detector will perform coincidence counting with all those detectors which are covered within its view angle, i.e. the angular range which this detector is able to detect. The coincidence counting circuit is connected to a pre-processing device not shown, and therefrom it is connected, via a signal transmission device 131 such as slip ring or via a cable, to a data processing device which, jointly with the scanner of the apparatus, constitutes positron emission computed tomographic apparatus.

The subject for examination 132 is placed on a bed 133, and is moved so that the required cross-sectional plane or slice plane for examination of this subject will be brought into agreement with the aforesaid plane in which the gamma ray detectors are arrayed. The bed-supporting base 134 is provided with wheels 135 for effecting such movement. Upon starting the electric motor 115, the rotation of this motor rotates the rotary frame 111 via the pulleys and the timing belt. Those positrons which are emitted from the isotopes administered into the body of the subject cause annihilation reaction with those electrons which are present nearby. Gamma rays which are generated in this way are irradiated into the gamma ray detectors. These gamma rays are detected by those gamma ray detectors which are coupled by the coincidence counting circuits to form a pair, and they are amplified by the pre-amplifiers. Whereupon, the coincidence counts are discriminated and the coincidence counting circuits deliver an output. These outputs are processed by the pre-processing device about such informations as those related to their sampling positions, and then they are inputted to a data processing device.

Each array of detectors is comprised of a plurality of detectors, and is arranged around the center of rotation in such way that at least one of the detectors in this array is disposed at an irregular position relative to the others of this array, and the respective arrays of detectors are arranged in such way that they will assume the position occupied by their adjacent array for each revolution through an angle of 360°/n (wherein: n represents an odd number of 3 or greater).

Description will be made below in further detail of such arrangement by referring to FIGS. 8 and 9.

Figure 8:
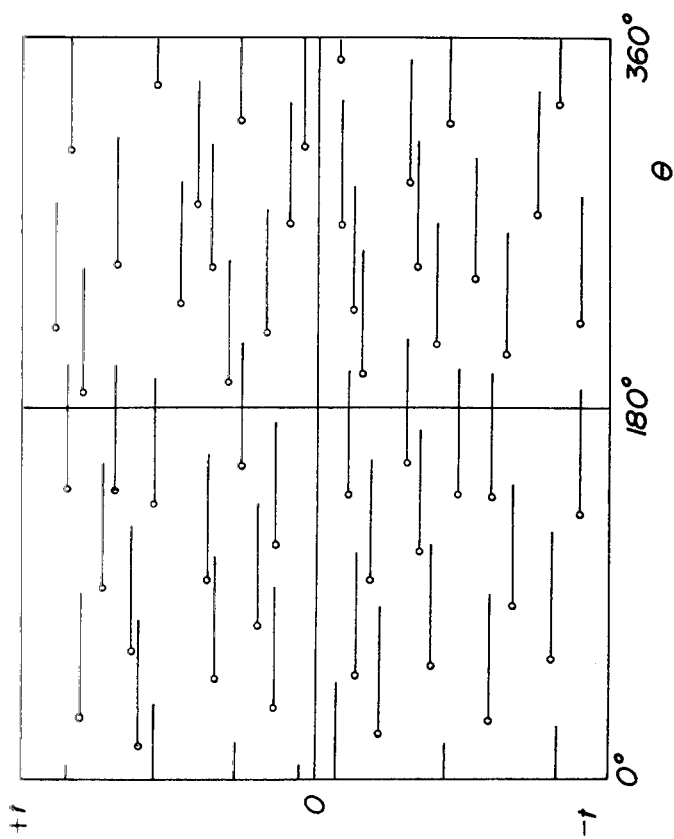

FIG. 8 shows an example of distribution of t, $\theta$. In this Figure which relates to a specific array of detectors, those sampling positions which are obtained without rotating this array of detectors are shown by small circles. When the array of detectors is rotated continuously through a certain angle, the sampling positions in the distribution chart of t, $\theta$ are expressed by a congregation of horizontally extending segments of lines as shown by solid lines in FIG. 8, and the length of each segment of line represents the extent of the angle of rotation. It should be understood that, in case the segment of a line passes beyond 360° in the right direction in the drawing, the remainder of the segment of the line is to be written in addition, starting at 0°.

In a CT scanner in general, a projection of a certain slice is identical with the projection extending in a direction opposite thereto by 180°. Accordingly in the distribution chart of t, $\theta$, the sampling positions within the extent of measurement angles 180°–360° can, as a whole, be rewritten into a distribution chart of t, $\theta$ of measurement angles of 0°–180° by writing, in addition, into the extent of measurement angles of 0°–180°. That is, by additionally writing the sampling positions shown in the angles of 180°–360° in the distribution chart of t, $\theta$ of FIG. 8 to that region of 0°–180° by inverting the symbol t, it is possible to express the entire distribution of t, $\theta$ in a manner as shown in FIG. 9. This corresponds to the fact that, in an ordinary X-ray CT scanner. The extent of measurement angle is sufficient if it is 180°.

Figure 9:
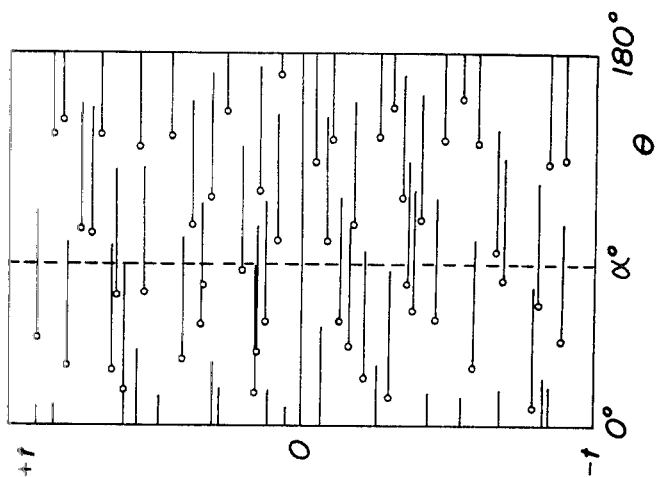
FIGS. 8 and 9 are charts of distribution of t, θ for explaining the arrangement of arrays of detectors in the apparatus of the present invention.

The sampling position for a given measurement angle $\theta$, for example $\alpha°$, is expressed as a point of intersection at which the vertical broken line crosses a horizontal segment of a line in FIG. 9. The density distribution, on the broken line, of the points of intersection corresponds to the sampling density distribution in this given measurement angle.

In case the arrays of detectors are rotated through 360°, those horizontal segments of lines which represent sampling positions extend to full extent in the horizontal axial direction in the t, $\theta$ distribution chart of FIG. 9. Therefore, the sampling densities for all of the respective measurement angles are identical.

In case, however, the extent of the revolution angle of the arrays of detectors is less than 360°, the horizontal solid lines in FIG. 9 which represent the extent of rotation angle will not diffuse through 0°–180°, and the sampling density distribution will vary depending on the angles of measurement. In a CT scanner, the measurement data of coincidence counting are, in general, subjected to compensation and adjustment by taken into consideration the non-uniformity of the sampling density distributions in the directions of measurement, and thereafter they are subjected to transverse image reconstruction processing. Accordingly, in case the sampling density distributions are identical for the respective directions of measurement, it is only necessary to first obtain this sampling density distribution, and then to use it to carry out the above-said compensation and adjustment. Therefore, the procedure is relatively simple. In case, however, the sampling density distributions are different depending on the measurement angles, as stated above, there is the need to first seek the respective sampling density distributions for the respective measurement angles, and then to compensate and adjust them.

As stated above, in the present invention, each of arrays of detectors is comprised of a plurality of detectors, and at least one detector in each array is disposed at an irregular position relative to the remainder detectors in this array. Such arrays of detectors are disposed around the center of rotation in such way that each array of detectors will assume the position occupied by the adjacent array for each revolution for an angle of 360°/n (wherein: n represents an odd number of 3 or greater). Whereby, even for a revolution through an angle less than 360°, it is possible to make identical the sampling density distributions for all the measurement angles.

For example, in case the arrays of detectors are arranged in such way that three same arrays are disposed, in side-by-side fashion, in the three sections which are defined, for each 120°, by half-lines extending from the center of rotation and forming respective angles of 120°, it is only necessary to rotate the arrays of detectors through 120° to obtain an identical sampling density distribution for all the directions of measurement. This will be understood to be clear from the fact that, since a same distribution is repeated for every angle of 120° in the distribution chart of t, $\theta$, all the horizontal segments of lines which represent sample positions are coupled in the horizontal direction, respectively.

The pattern of arrangement of detectors can be made arbitrarily as desired, and it may be a circle defined around a center of rotation serving as the center of the circle. However, a greater liberty for obtaining an optimum arrangement can be obtained, in general, from a pattern other than a circular arrangement.

An irregular positioning of a detector or detectors in an array may be effected either by altering the intervals of at least one detector between its adjacent detectors relative to the interval between the other detectors of this array, or by altering the distance of at least one detector of the array from the center of rotation relative to such distance of the other detectors of the array, or by altering both the above-said intervals and distance of at least one detector of the array relative to those of the other detectors of the array.

It should be understood that n represents an odd number of 3 or greater. This n, however, requires to be $\frac{1}{2}$ or smaller than the total number of the detectors provided, however great it may be intended to set the value of n. This limitation is based on the consideration that, in detector arrays which are arranged so that each array will assume the position of its adjacent array for each revolution through an angle of 360°/n, the pattern of detector arrangement which is rotated repeatedly n times requires that at least one of the detectors in each array be disposed irregularly relative to the remainder detectors in each array, so that each array requires to include at least two detectors.

In case n is an even number, it will be noted that, because the position of an array of detectors, after a revolution through an angle of 180°, will be brought into agreement with the position of another array prior to the revolution, the value of t which is produced by the detectors located 180° opposite to a certain detector will be confined to t=0, resulting in an increase in the data of those samples of t=0, so that it is impossible to make fine the sampling density in the remaining portions.

In case those detectors which constitute an array of detectors has at least one detector which is positioned irregularly relative to the other detectors in the array and in case all of these detectors are positioned at an equal distance from the central axis of rotation, it is desirable to set the radius of the measurement visual field small in order to avoid the confinement of the values of t. The value of t at point of confinement in such case is shown by the following formula:

$$t_0 = R\cos\left(180° \cdot \frac{m}{n}\right) \quad (4)$$

wherein: R represents the radius of said circle; and m represents an integer smaller than n.

For example, in case n=3, sample positions gather at m=1, and m=2. The value of t of such sample positions will be given from Formula (4) respectively as follows:

$$t_1 = R\cos\left(\frac{180°}{3}\right) = R/2$$

$$t_2 = R\cos\left(\frac{180° \times 2}{3}\right) = -R/2.$$

However, by limiting the measurement visual field radius to slightly smaller than one half of the radius of the detector arrays, and from the fact that the portion of confinement of sample position shown by the above-mentioned formula is not used, there is obtained a sample of a good uniformity even in the case of n=3. Furthermore, in cases of n=5, 7, ... also, good uniformity can be attained by somewhat narrowing the measurement visual field.

FIG. 10 shows a concrete example of detector arrangement. This detector arrangement is comprised of a plurality of detectors, and three sets of detector arrays a, b and c, which each contains some detectors disposed irregularly relative to the other detectors in each array by changing the intervals of these some detectors relative to the intervals of the other detectors, are disposed around the center C of rotation in such way that each set of detector array will assume the position occupied by its adjacent detector array for each revolution through the angle of 360°/3.

More particularly, detector arrays are each compurised of twenty-two (22) detectors 121. Each of these detectors is disposed at a same distance from the center C of rotation. In other words, the detectors are arranged on a circle or arc concentric with the center of rotation. However, those detectors including the first one to the 12th one (these numbers are shown in Arabic number for the respective detectors in FIG. 10) are spaced from each other at each central angle of 5°, whereas those detectors including the 11th one to the 22nd one are spaced from each other at a central angle of 6°.

Figure 11:
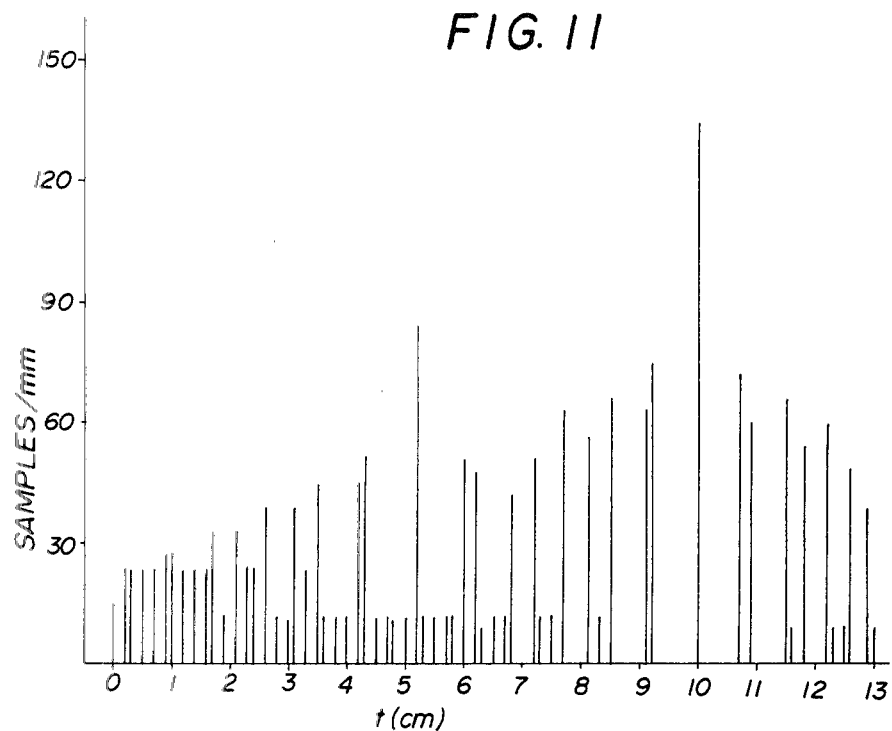
FIG. 11 is a chart showing a distribution of sampling density obtained by the arrangement shown in FIG. 10.

FIG. 11 shows the sampling density distribution obtained from the detector arrangement shown in FIG. 10.

In the sampling density distribution shown, the horizontal axis represents t, and the vertical axis indicates the number of sampling positions within the range of width of 1 mm of t, i.e. the sampling density with respect to t. The sampling interval with respect to θ can be reduced by the rotary scanning, as stated previously. On the basis of rotary scanning, it may be said that the largeness of the sampling interval determines the quality of the scanning mechanism. The horizontal axis indicates the distance from the center of rotation of the detector, i.e. from the center of effective field of view. Therefor, if there is a segment (bar graph) showing the presence of a projection of a number of samples at the position 5 cm on the horizontal axis, this will indicate a sufficient sampling of the informations concerning the radioisotopes which are located on the circular circumference of a radius of 5 cm. If, however, there is no segment at the position of 5.5 cm, the data on the circular circumference indicate the absence of at least those samplings which are depicted as rectilinear lines tangential with this circular circumference. In case a distribution of such pattern of presence and absence of segment on the horizontal axis is repeated, this will mean that samplings with respect to t are conducted skipwise and coarsely. On the other hand, in case segments of a same length are arrayed densely on the horizontal axis, this means that the informations concerning all the positions lying within the field of view are collected uniformly with no unevenness, indicating that the scanning mechanism is the most desirable one.

It should be understood that the sampling density distributions employed in the present invention are based on the consideration that, unless specifically designated, the distance between the detectors and the center of rotation is selected to be 20 cm. No description is made of calculation of sampling density distribution. Such calculating, however, will be apparent for those skilled in the art.

By referring to this sampling density distribution chart, it will be understood clearly that the sampling intervals obtained by the detector arrangement according to the present invention will be as small as 2–3 mm and that t can take more different values. In a detector arrangement wherein the respective detectors are disposed at a uniform distance from the center of rotation, and the intervals between the detectors are identical, however, there are provided sixty-four (64) detectors, and the distance between these detectors and the center of rotation is selected at 20 cm. In case sampling is taken, for each rotation, in the vicinity of a rotation angle of about 2.81°, the sample intervals will be about 12.7 mm.

Figure 12:
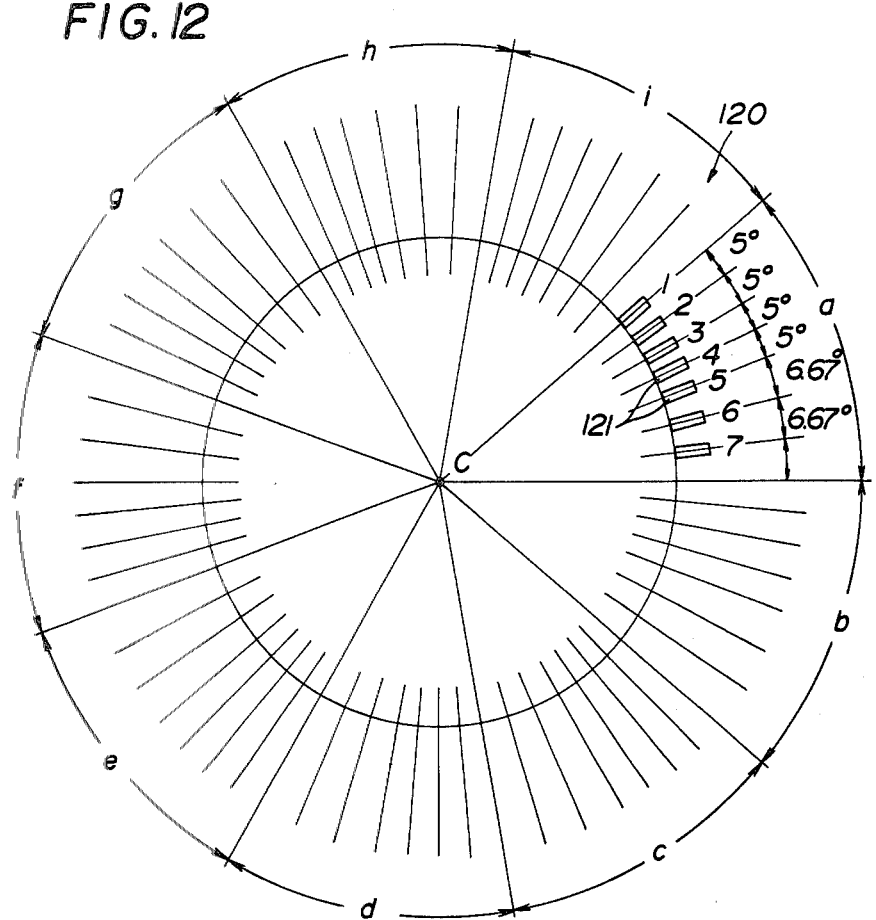
FIG. 12 is an explanatory illustration showing another arrangement of arrays of detectors, embodying the present invention.
Figure 13:
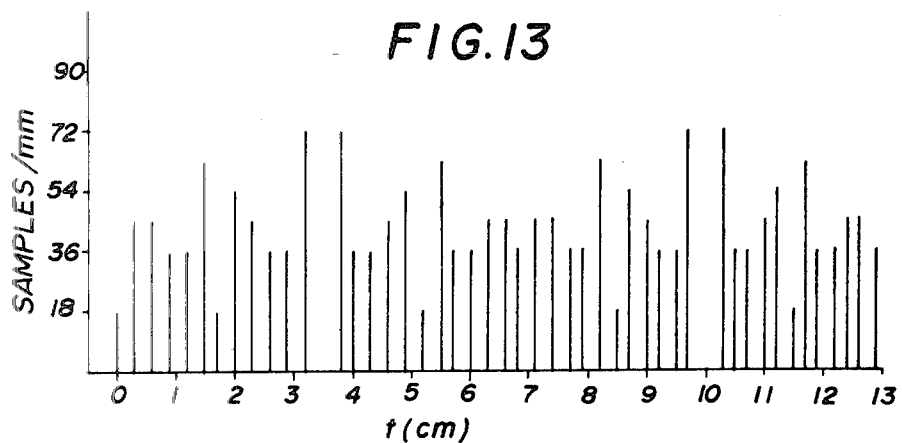
FIG. 13 is a chart showing a distribution of sampling density obtained by the arrangement shown in FIG. 12.

FIG. 12 shows another arrangement of detector arrays. The detector arrangement is constituted by nine detector arrays a, b, ... and i which will assume the position of their adjacent array for each revolution through an angle of 360°/9. Each detector array is comprised of seven (7) detectors 121. The respective detectors are disposed at a uniform distance from the center C of rotation. However, the first to the fourth detectors are each spaced apart at 5° of central angle, whereas the fourth to the seventh detectors are each spaced at a central angle of 6.67°. FIG. 13 shows the sampling density distribution obtained from this detector arrangement.

Figure 15:
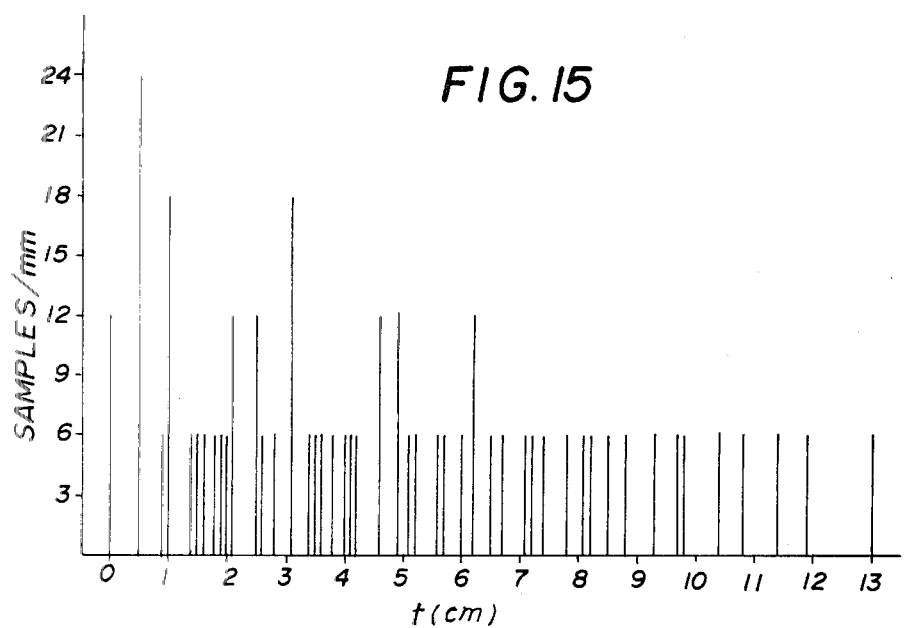
FIG. 15 is a chart showing a distribution of sampling density obtained by the arrangement shown in FIG. 14.
Figure 14:
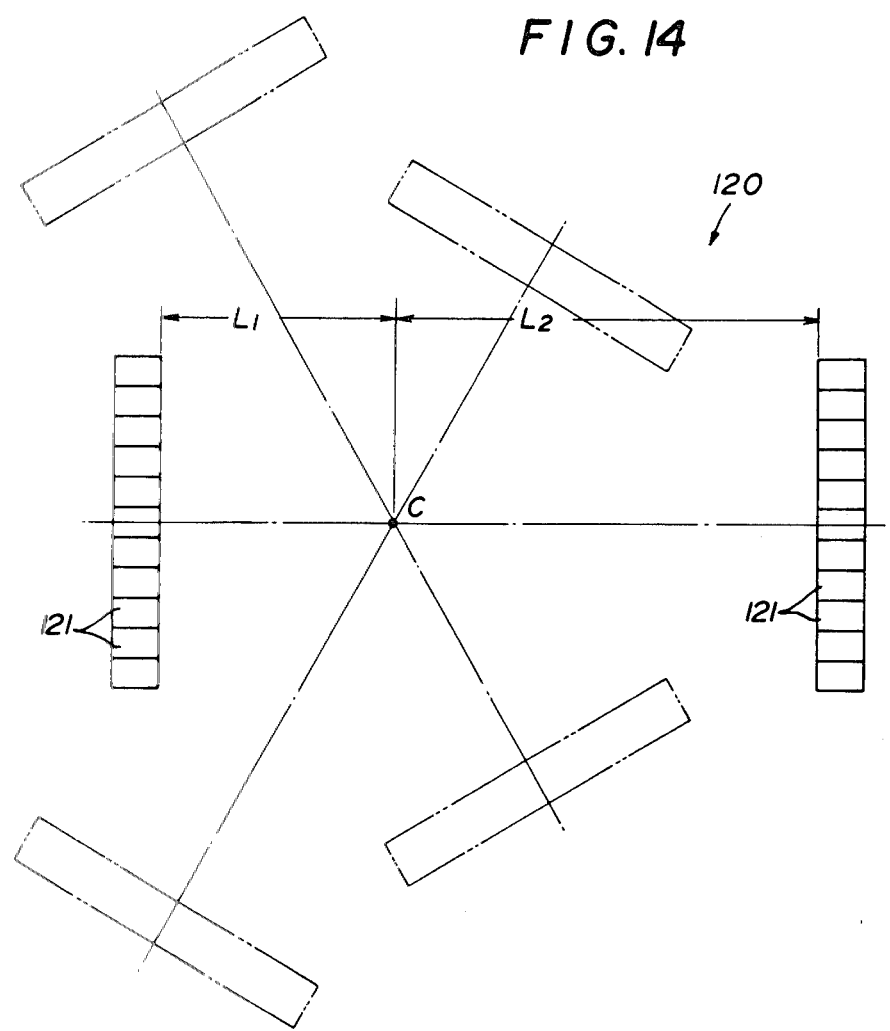
FIG. 14 is an explanatory illustration showing still another embodiment of arrays of detectors, embodying the present invention.

FIG. 14 shows still another arrangement of detector arrays. A certain detector array a is comprised of detector pair which are arranged in parallel with each other relative to the center C of rotation. It should be noted that the distance $L_1$ between those detectors in one of the pair and the center C of rotation is different from that $L_2$ of the other pair. Each of the pair includes eleven (11) detectors which are disposed at a uniform interval relative to each other. Such pair of detector arrays are provided in three pairs around the center of rotation in such way that they will assume the position occupied by their adjacent pair for each revolution through an angle of 360°/3. The remaining two pairs of detector arrays are indicated by two-dot chain lines in FIG. 14. FIG. 15 shows the sampling density distribution obtained from the arrangement of FIG. 14.

Figure 16:
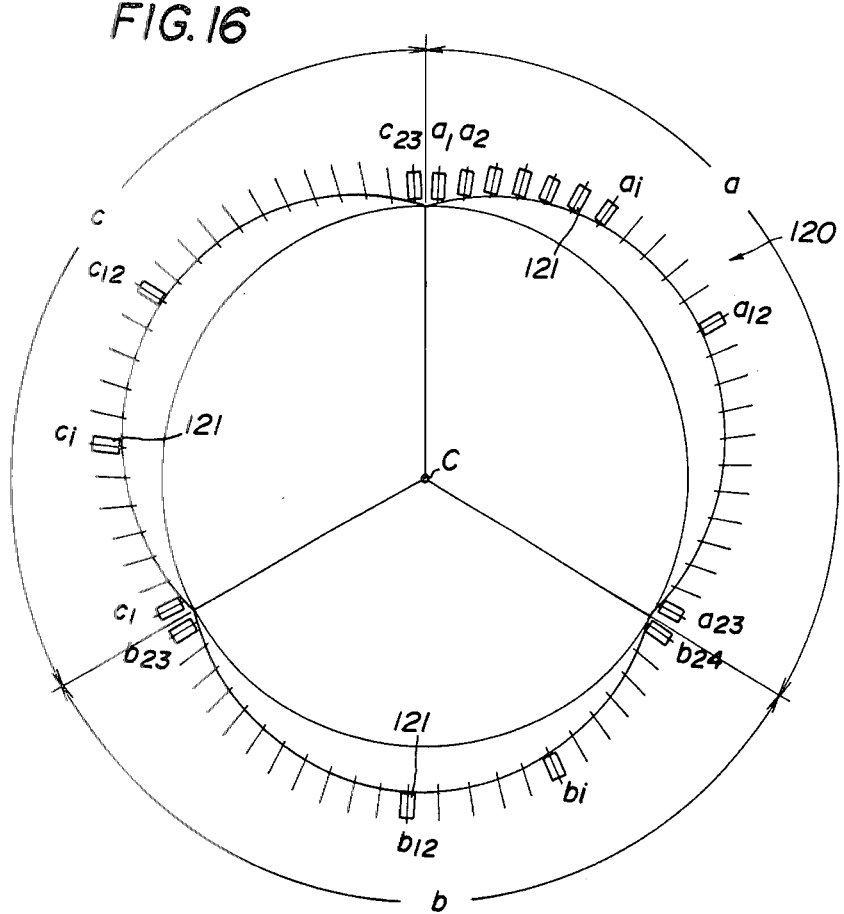
FIG. 16 is an explanatory illustration showing yet another arrangement of arrays of detectors, embodying the present invention.
Figure 17:
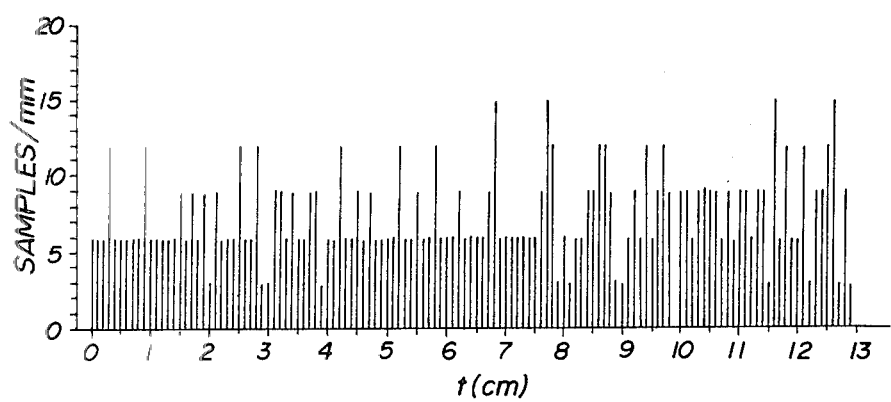
FIG. 17 is a chart showing a distribution of sampling density obtained by the arrangement shown in FIG. 16.

FIG. 16 shows a concrete arrangement of arrays of detectors 120. The detector arrangement is comprised of three detector arrays a, b and c which each has an identical arrangement of detectors. These respective detector arrays are assembled for every angle of 120°. In other words, this represents an n=3 arrangement. Each array includes 23 detectors. The i-th detectors in the respective arrays a, b and c, i.e. detector $a_i$, $b_i$ and $c_i$, are disposed at an identical distance from the center C of rotation, and they are positional at every angle of 120°. Accordingly, the pattern of arrangement is such that the angular spacing of the first to the 12th detectors in which i is contained and which are located on three portions which bulge progressively in three different directions from a circular circumference as noted in FIG. 16 are spaced at an angle of 60°/11. The other detectors are spaced at an angle of 60°/12. Also, the distance between the i-th detector and the center of rotation will increase progressively with an increase in the number of i at a pitch of 2d/11 (wherein: d represents the interval of the 12th–23rd detectors containing i) and will become maximum when i=12. Thereafter, the distance decreases progressively at the pitch of d/6. The apparent radius of the pattern for the arrangement of detectors is about 20 cm. The sampling density which is obtained when this arrangement is rotated through 120° is constant for all angles of measurement. This sampling density distribution which is expressed by $t_k$ of every 1 mm is shown in FIG. 17. In case detectors are arranged on a circular circumference, there ought to occur a confinement of sample position at a site representing one half of the radius of this circle, i.e. at the site of t=10 cm.

In FIG. 17, however, it can be noted that sufficiently fine sampling is carried out in the vicinity of t=10 cm.

Even in case of a scanning angle of rotation is less than 360°, there is some degree of liberty in the pattern of arrangement of detectors. That is, detectors may be arranged in accordance with a certain geometrical law as shown in FIG. 16. However, determination of arrangement may be done in a trial-and-error fashion, or by using an electronic computer.

The determination of arrangement of detectors by the use of an electronic computer is as follows. Firstly, a certain arrangement is given, and the distribution of its sampling density is obtained. Then, appropriate indices showing the fineness of its distribution and showing the uniformity are defined. The locations of the respective detectors are adjusted one after another so that starting from an arbitrary arrangement such as arrangement with equal spacing, and finally reaching the level that said indices become maximum, and thus the locations of all the detectors are corrected, and furthermore such process is repeated again and again, and this is called "sequential search method". These indices are, for example, FOM which is obtained from the following formula:

$$FOM = 1/\sqrt{\sum_k \left(\frac{1}{s(t_k)}\right) \sum_k s(t_k)} \quad (5)$$

wherein $t_k$ represents a digitalized value of t obtained by separating the value of t at a certain interval, $s(t_k)$ represents a sampling density distribution which is expressed as a function of $t_k$, and the symbol $\Sigma$ means an addition to be made with respect to the extent of $t_k$ which, in turn, is determined by a necessary field of view of measurement. Furthermore, the pattern in which the detectors are arranged may be selected by such means as an electronic computer. For example, the angles defined between the locations of the respective detectors and a reference line, as well as the distances of the detectors from the center of rotation may be considered to be variable to a certain extent. On the other hand, those limitations accruing from other mechanical and/or physical conditions, for example the minimum interval allowed between adjacent detectors, the maximum value and the minimum value of the distance between the detectors and the center of rotation, are set, and in the same way as that stated above, two-dimensional arrangement of all the detectors may be determined by such means as the sequential search method.

The following Table 1 shows the positional angles of the respective detectors, representing an embodiment, which positional angles being determined by sequential search method using an electric computer.

TABLE 1

| No. of detector | Positional angle(°) | No. of detector | Positional angle(°) | No. of detector | Positional angle(°) |
|---|---|---|---|---|---|
| 1 | 5.200 | 21 | 109.800 | 41 | 215.000 |
| 2 | 10.850 | 22 | 114.850 | 42 | 220.000 |
| 3 | 16.500 | 23 | 119.700 | 43 | 224.900 |
| 4 | 22.000 | 24 | 125.200 | 44 | 229.800 |
| 5 | 27.100 | 25 | 130.850 | 45 | 234.850 |
| 6 | 32.727 | 26 | 136.500 | 46 | 239.700 |
| 7 | 38.227 | 27 | 142.000 | 47 | 245.200 |
| 8 | 43.627 | 28 | 147.100 | 48 | 250.850 |
| 9 | 49.182 | 29 | 152.727 | 49 | 256.500 |
| 10 | 54.641 | 30 | 158.227 | 50 | 262.000 |
| 11 | 60.091 | 31 | 163.627 | 51 | 267.100 |
| 12 | 64.850 | 32 | 169.182 | 52 | 272.727 |
| 13 | 70.000 | 33 | 174.641 | 53 | 278.227 |
| 14 | 75.000 | 34 | 180.091 | 54 | 283.627 |
| 15 | 80.000 | 35 | 184.850 | 55 | 289.182 |
| 16 | 85.000 | 36 | 190.000 | 56 | 294.641 |
| 17 | 90.000 | 37 | 195.000 | 57 | 300.091 |
| 18 | 95.000 | 38 | 200.000 | 58 | 304.850 |
| 19 | 100.000 | 39 | 205.000 | 59 | 310.000 |
| 20 | 104.900 | 40 | 210.000 | 60 | 315.000 |
| 61 | 320.000 | 64 | 335.000 | 67 | 349.800 |
| 62 | 325.000 | 65 | 340.000 | 68 | 354.850 |

TABLE 1-continued

| No. of detector | Positional angle(°) | No. of detector | Positional angle(°) | No. of detector | Positional angle(°) |
|---|---|---|---|---|---|
| 63 | 330.000 | 66 | 344.900 | 69 | 359.700 |

Figure 18:
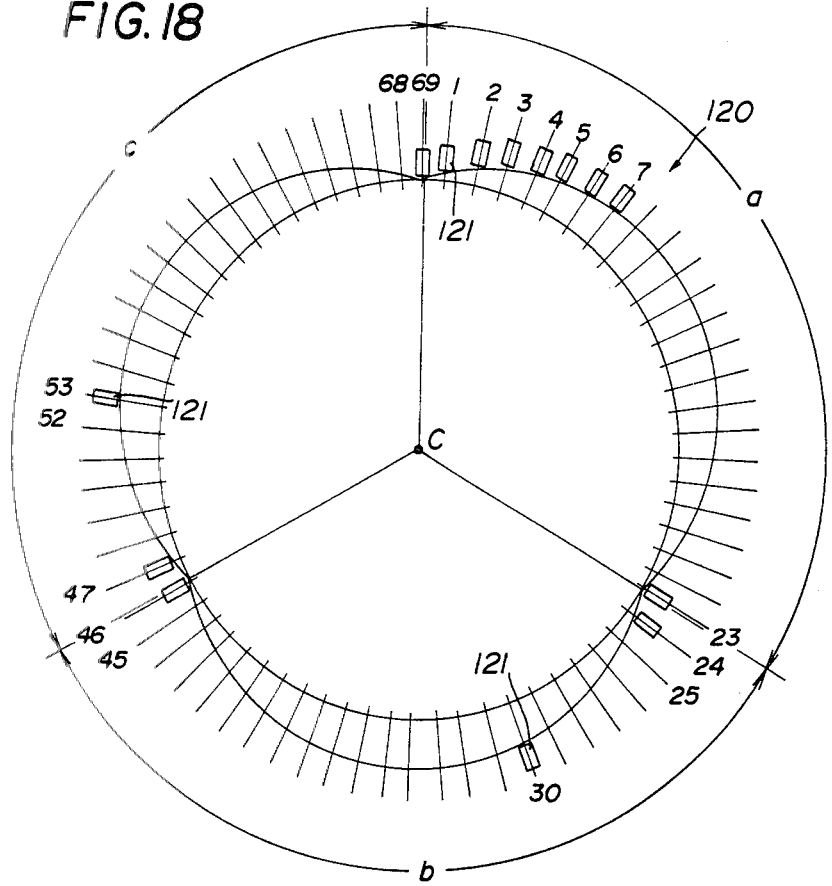
FIG. 18 is an explanatory illustration showing a further arrangement of arrays of detectors, embodying the present invention.
Figure 19:
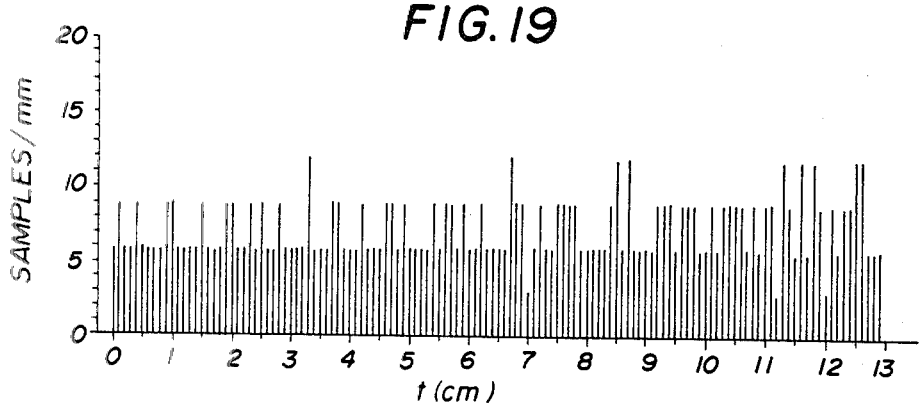
FIG. 19 is a chart showing a distribution of sampling density obtained by the arrangement shown in FIG. 18.

FIG. 18 shows a detector arrangement made in accordance with Table 1. The total number of the detectors and the pattern of detector arrangement are identical with those in the embodiment of FIG. 16. This arrangement, however, is determined by starting from the arrangement shown in FIG. 16, while modifying the positional angles of the respective detectors little by little, and through sequential search step by step so that the indices (FOM) shown in Formula (5) concerning the sampling density distribution sought with respect to $t_k$ for every 1 mm will become maximum. The minimum angular interval allowable between the respective adjacent detectors, however, is set at 4.5°. FIG. 19 shows the sampling density distribution obtained by this detector arrangement. When compared with the result shown in FIG. 17, it will be clearly noted that the uniformity of sampling density distribution is further improved.

Description has hereinabove been made of embodiments arranged so as to obtain an image of a single slice. It should be noted, however, that images of a plurality of slices can be obtained also at the same time by providing, in a plurality of stages along the center axis of rotation, sets of detector arrays which, in each set, are disposed in a plane, in such manner as shown in FIGS. 20 and 21. More particularly, reference numerals 120a, 120b, 120c and 120d represent detector arrays provided in four stages, each stage being arranged in a plane perpendicular to a common rotation axis C–C'. These detector arrays of four stages are adapted to rotate about this rotation axis. In such instance, it should be understood that coincidence counting can be taken not only between the arranged detectors in each stage, but also between those detectors in adjacent stages, and thus the detection efficiency is further enhanced.

Furthermore, as shown in FIG. 22, there may be provided, along a plurality of planes perpendicular to the rotation axis C–C', a number of gamma-ray-position detectors. For example, on paired crystal bodies 122 which are each of an elongated configuration in the direction of the rotation axis, there are arranged, in a plurality of stages, photo-multiplier tubes 123 to construct a plurality of stages of detector arrays for detecting the positions of gamma rays generated. By rotating these detector arrays about the rotation axis C–C', it is possible to obtain the images of slices of multiple stages. More particularly, it is possible to detect the positions $X_1, X_2 \ldots$ of incident gamma rays with respect to the direction parallel with the rotation axis C–C'. By utilizing the resulting informations, it is possible to carry out a simultaneous measurement of the images of multiple stages. In such instance also, the detector arrangement and the manner of rotation of the detector arrays according to the present invention as described above are extremely useful in obtaining a fine sampling density.

It should be noted also that the rotation of the arrays of detectors need not be done in continuous fashion. The rotation may be performed in fine stepwise fashion, and measurement data may be collected for a given period of time in each period of time.

Furthermore, the detector arrays may be rotated in reciprocal fashion, that is the rotation may be reciprocal rotation through an angle of 360°/n. In such instance, however, it is desirable to perform rotation at a constant speed for each period in which data are collected. The rotation, however, may be that of non-uniform speeds. In such instance, the sampling density distribution will become different for use angle of measurement. Thus, there will be needed amendments and corrections for the data thus obtained in correspondence with the angular velocity employed.

What is claimed is:

1. An apparatus for performing positron emission computed tomography, comprising:
   n revolvable detector arrays where n is an odd number equal to at least three, each array including a plurality of detectors where there is a fixed spacing between each detector of each array and the remaining detectors of that array,
   each array containing at least one detector disposed at an irregular position relative to other detectors in said array,
   said n revolvable detector arrays being successively arranged around a center of revolution where each array has an adjacent array on each side of it and where the relative locations of the detectors with respect to each other are the same for each array so that, for each revolution of the n detector arrays through an angle of 360°/n, the detectors of each array will assume respectively positions previously assumed by the detectors of one of its adjacent arrays.

2. An apparatus according to claim 1, in which:
   said irregular position of at least one detector is brought about by altering intervals between this detector and its adjacent detectors.

3. An apparatus according to claim 1, in which:
   said irregular position of at least one detector is brought about by altering a distance between this detector and the center of rotation.

4. An apparatus according to claim 1, in which:
   said irregular position of at least one detector is brought about by altering a distance between this detector and the center of rotation and by altering intervals between this detector and its adjacent detectors.

5. An apparatus according to any one of claims 1 to 4, in which:
   the arrays of detectors are provided in multiple stages, permitting coincidence counting to be performed between those detectors in arrays in one of the stages and between those detectors in arrays of adjacent stages.

* * * * *